US012678385B2

(12) United States Patent　(10) Patent No.: US 12,678,385 B2
Lu　(45) Date of Patent:　Jul. 14, 2026

(54) NAIL POLISH GLUE AND PREPARATION METHOD AND APPLICATION THEREOF

(71) Applicant: Yang Lu, Guangzhou (CN)

(72) Inventor: Yang Lu, Guangzhou (CN)

( * ) Notice: Subject to any disclaimer, the term of this patent is extended or adjusted under 35 U.S.C. 154(b) by 442 days.

(21) Appl. No.: 18/129,103

(22) Filed: Mar. 31, 2023

(65) Prior Publication Data

US 2024/0130943 A1　Apr. 25, 2024
US 2024/0225977 A9　Jul. 11, 2024

(30) Foreign Application Priority Data

Oct. 25, 2022　(CN) ......................... 202211326937.9

(51) Int. Cl.
　*A61K 8/46*　(2006.01)
　*A61K 8/37*　(2006.01)
　*A61K 8/49*　(2006.01)
　*A61K 8/55*　(2006.01)
　*A61K 8/85*　(2006.01)
　*A61Q 3/02*　(2006.01)

(52) U.S. Cl.
　CPC ................. *A61K 8/46* (2013.01); *A61K 8/37* (2013.01); *A61K 8/49* (2013.01); *A61K 8/55* (2013.01); *A61K 8/85* (2013.01); *A61Q 3/02* (2013.01); *A61K 2800/43* (2013.01); *A61K 2800/81* (2013.01); *A61K 2800/95* (2013.01)

(58) Field of Classification Search
　None
　See application file for complete search history.

(56) References Cited

U.S. PATENT DOCUMENTS

2019/0351262 A1* 11/2019 Landa ..................... B31D 1/021

FOREIGN PATENT DOCUMENTS

CN　105878054 A　* 8/2016 ........... A61K 8/8152

OTHER PUBLICATIONS

English translation of CN-105878054-A (Year: 2016).*

* cited by examiner

*Primary Examiner* — Nicole P Babson
(74) *Attorney, Agent, or Firm* — Bayramoglu Law Offices LLC

(57)　ABSTRACT

A nail polish glue and a preparation method and application thereof are provided. The nail polish glue includes the following components in parts by weight: 15-57 parts of an acrylate prepolymer, 20-52 parts of an acrylate active monomer, 5-10 parts of a photoinitiator, 5-10 parts of mercaptan, 5-10 parts of an additive, and 3-8 parts of a colorant. The nail polish glue of the present disclosure has low odor and environmental friendliness, is convenient to operate and package, can be directly applied without using a primer and a seal, and has the adhesion of the primer and the gloss retention of the seal. Through reasonable collocation and mutual complement of the amount of components, excellent mechanical properties including hardness, adhesion and wear resistance, which are significantly improved, are effectively achieved.

20 Claims, No Drawings

NAIL POLISH GLUE AND PREPARATION METHOD AND APPLICATION THEREOF

CROSS REFERENCE TO THE RELATED APPLICATIONS

This application is based upon and claims priority to Chinese Patent Application No. 202211326937.9, filed on Oct. 25, 2022, the entire contents of which are incorporated herein by reference.

TECHNICAL FIELD

The present disclosure relates to the technical field of beautifying of nails, and in particular to a nail polish glue and a preparation method and application thereof.

BACKGROUND

At present, with continuous development and innovation of nail beautifying technologies, more and more nail beautifying products are produced on the market. Due to the enrichment of the nail beautifying products, the nail beautifying industry can be flourishing continuously, and more economic benefits are brought.

Nail polish glues have been widely used in the nail beautifying industry in recent years. Compared with traditional nail polishes, the nail polish glues have the characteristics of environmental friendliness, no toxicity, health, and safety. In addition, the nail polish glues have common advantages of glues and nail polishes, and have full and clear colors and longer-lasting glosses, so that the nail polishes have been gradually replaced with the nail polish glues. However, current nail polish glues still have the following problems:

1) primers, nail polish glues, and seals are required to be applied during use, the whole operation process is complicated and has many procedures, and the operation by a professional manicurist is required to achieve a good effect; and 2) all the glues are flowing liquids, and each variety is required to be separately packaged in order to avoid mixing of the glues.

In view of this situation, it is necessary to provide a technical scheme to solve the above problems.

SUMMARY

In order to overcome the defects of the prior art, a first objective of the present disclosure is to provide a nail polish glue. The nail polish glue is solid and convenient to package and store, and can be directly applied without using a primer and a seal. Moreover, the nail polish glue has the adhesion of the primer and the gloss retention of the seal, and is convenient to operate.

A second objective of the present disclosure is to provide a preparation method of the nail polish glue.

A third objective of the present disclosure is to provide application of the nail polish glue in beautifying of nails.

The first objective of the present disclosure is realized by using the following technical scheme.

A nail polish glue is characterized by including the following components in parts by weight: 15-57 parts of an acrylate prepolymer, 20-52 parts of an acrylate active monomer, 5-10 parts of a photoinitiator, 5-10 parts of mercaptan, 5-10 parts of an additive, and 3-8 parts of a colorant.

Preferably, the acrylate prepolymer is at least one selected from the group consisting of polyurethane acrylate, pure acrylate, and polyester acrylate.

Preferably, the acrylate active monomer is at least one selected from the group consisting of hydroxyethyl methacrylate, acryloyl morpholine, isobornyl acrylate, dipropylene glycol diacrylate, 1,6-hexadiol diacrylate, and cyclic trimethylopropane formal acrylate.

Preferably, the photoinitiator is at least one selected from the group consisting of acylphosphorus oxide, 1-benzoyl-cyclohexanol, 2-methyl-1-(4-methylthiophenyl)-2-morpho-line-1-acetone, and ethyl (2,4,6-trimethylbenzoyl)phe-nylphosphinate.

Preferably, the mercaptan is at least one selected from the group consisting of pentaerythritol tetra(3-mercaptopropi-onate), trimethylolpropane tris(3-mercaptopropionate), and 1,4-butanediol di(3-mercaptopropionate).

Preferably, the additive is at least one selected from the group consisting of an anti-settling agent, a dispersing agent, a leveling agent, a thickening agent, a defoaming agent, microcrystalline cellulose, and microcrystalline wax.

The second objective of the present disclosure is realized by using the following technical scheme.

A preparation method of the nail polish glue includes the following steps:

S1, subjecting the acrylate prepolymer, the acrylate active monomer, the photoinitiator, and the mercaptan to mixing, heating, and stirring to obtain a first mixture;

S2, adding the additive to the first mixture, and conducting stirring for a dispersion to obtain a second mixture; and S3, adding the colorant to the second mixture for a color adjustment, and conducting grinding, filtration, baking at a constant temperature, and standing to obtain the nail polish glue.

Preferably, in step S1, the heating is conducted at a temperature of 45-60° C., and the stirring is conducted at a rotation speed of 500-800 r/min for 10-20 minutes. In step S2, the stirring for the dispersion is conducted at a rotation speed of 1,000-1,500 r/min for 60-80 minutes.

Preferably, in step S3, the baking is conducted at a constant temperature of 60-80° C. for 2-4 hours.

The third objective of the present disclosure is realized by using the following technical scheme.

Application of the nail polish glue in beautifying of nails includes using the nail polish glue in beautifying of nails.

Compared with the prior art, the present disclosure has the following beneficial effects.

1. The nail polish glue of the present disclosure has low odor and environmental friendliness, is convenient to operate and package, can be directly applied without using a primer and a seal, and has the adhesion of the primer and the gloss retention of the seal. Through reasonable collocation and mutual complement of the amount of components, excellent mechanical properties including hardness, adhesion and wear resistance, which are significantly improved, are effectively achieved.

2. The nail polish glue of the present disclosure is solid in the case of no external force, and is convenient to package and store. Each variety is not required to be separately packaged. Under stirring of an external force, the viscosity of the glue can be rapidly reduced. The glue is convenient to apply, and has a high curing speed and a mirror leveling effect. A cured film has adhesion on nails and high gloss and color retention.

3

3. The nail polish glue can be prepared by the preparation method of the nail polish glue of the present disclosure. The preparation method is simple in process and applicable to large-scale application.

DETAILED DESCRIPTION OF THE EMBODIMENTS

The technical schemes of the present disclosure are clearly and completely described below in conjunction with specific embodiments. Apparently, the embodiments described are merely a part of the embodiments of the present disclosure, rather than all of the embodiments. Based on the embodiments of the present disclosure, all other embodiments obtained by a person of ordinary skill in the art without making creative effort are within the protection scope of the present disclosure.

In a first aspect of the present disclosure, a nail polish glue is provided. The nail polish glue includes the following components in parts by weight: 15-57 parts of an acrylate prepolymer, 20-52 parts of an acrylate active monomer, 5-10 parts of a photoinitiator, 5-10 parts of mercaptan, 5-10 parts of an additive, and 3-8 parts of a colorant.

The nail polish glue of the present disclosure has low odor and environmental friendliness, is convenient to operate and package. For example, unified packaging of multiple colors or multiple bottles of the glue in an eyeshadow plate can be used. The nail polish glue is solid, and mixing by flowing of the glue cannot be caused. The nail polish glue has a high curing speed, good adhesion, a high gloss and other characteristics. Although being solid, the glue can recover a good leveling property without a brushmark after being applied, can be completely cured after irradiation under a 36 W UV/LED lamp for 60 seconds, and has a mirror leveling effect. A cured film has adhesion on nails, wear resistance, chemical resistance, and high gloss and color retention.

In one of the embodiments, a nail polish glue is provided. The nail polish glue includes the following components in parts by weight: 20-50 parts of an acrylate prepolymer, 25-45 parts of an acrylate active monomer, 6-8 parts of a photoinitiator, 6-8 parts of mercaptan, 6-8 parts of an additive, and 4-6 parts of a colorant.

Further preferably, a nail polish glue is provided. The nail polish glue includes the following components in parts by weight: 25-35 parts of an acrylate prepolymer, 30-40 parts of an acrylate active monomer, 6-8 parts of a photoinitiator, 6-8 parts of mercaptan, 6-8 parts of an additive, and 4-6 parts of a colorant.

In one of the embodiments, the acrylate prepolymer is a composition of more than one or two of polyurethane acrylate, pure acrylate, or polyester acrylate.

Since a molecule of the polyurethane acrylate contains an acrylic functional group and a carbamate bond, a cured adhesive has high wear resistance, adhesion, flexibility, high peeling strength and excellent low temperature resistance of polyurethane and excellent optical properties and weather resistance of polyacrylate. The polyurethane acrylate contains many polar groups such as an ester group and amino, and can achieve a hydrogen bonding effect with an anti-settling agent, namely fumed silica, so that the thixotropy of a system is improved. In addition, a short-chain ternary alcohol is used to replace a part of diols, so that the synthesized polyurethane acrylate has a rigid branched structure, a high curing rate, high hardness, and better adhesion.

The polyester acrylate has the excellent properties of low odor, low irritation, high reactivity, good flexibility and pigment wettability. A carboxyl contained can achieve a hydrogen bonding effect with the anti-settling agent, namely fumed silica, so that the thixotropy of the system is improved.

Further preferably, the polyurethane acrylate is aliphatic carbamate acrylate.

In one of the embodiments, the acrylate active monomer is a composition of more than one or two of hydroxyethyl methacrylate, acryloyl morpholine, isobornyl acrylate, dipropylene glycol diacrylate, 1,6-hexadiol diacrylate, or cyclic trimethylopropane formal acrylate.

The acrylate active monomer mainly has the effects of realizing dilution, increasing the crosslinking density and increasing the reaction speed.

In one of the embodiments, the photoinitiator is a composition of more than one or two of acylphosphorus oxide, 1-benzoylcyclohexanol, 2-methyl-1-(4-methylthiophenyl)-2-morpholine-1-acetone, or ethyl (2,4,6-trimethylbenzoyl) phenylphosphinate.

The photoinitiator is excited by ultraviolet light to produce free radicals, instantly resulting in a crosslinking reaction of the acrylate prepolymer and the acrylate active monomer, and the curing speed is increased.

In one of the embodiments, the mercaptan is a composition of more than one or two of pentaerythritol tetra(3-mercaptopropionate), trimethylolpropane tris(3-mercapto-propionate), or 1,4-butanediol di(3-mercaptopropionate).

The nail polish glue is affected by oxygen inhibition in a curing process, so that the curing time is prolonged. The mercaptan has the effects of resisting oxygen inhibition and promoting surface curing, so that the phenomenon of oxygen inhibition can be effectively eliminated.

In one of the embodiments, the additive is a composition of more than one or two of an anti-settling agent, a dispersing agent, a leveling agent, a thickening agent, a defoaming agent, microcrystalline cellulose, or microcrystalline wax.

The anti-settling agent is used as a rheological control agent of a coating material, so that the coating material has thixotropy and greatly improved viscosity. Fumed silica is used as the anti-settling agent.

The dispersing agent can be used for improving the gloss of the nail polish glue, improving the tinctorial strength and hiding power, improving the coloring strength and toning property, preventing a floating color and a drifting color of the nail polish glue, and preventing flocculation and settlement. By adding the dispersing agent, the tinctorial strength, rheological property, stability and other properties of pigment particles in a dispersion system can be significantly improved. One of polyether modified siloxane or a polymer copolymer containing a pigment affinity group is selected as the dispersing agent.

By adding the leveling agent, the surface tension of the nail polish glue can be significantly reduced, the wetting ability and fluidity of the nail polish glue are improved, phenomena of a floating color and a flower-like color are effectively reduced, and properties such as leveling property, smoothness, shrinkage hole resistance, wear resistance, scratch resistance and peeling resistance of the nail polish glue can also be improved, so that the nail polish glue has a mirror leveling effect after curing. Glide 450 or Glide 410 of Tego of Germany is used as the leveling agent.

In one of the embodiments, the colorant is a composition of more than one or two of CI 77491, CI 77492, CI 77510, CI 77891, CI 77289, or CI 77266. Due to the colorant, the nail polish glue can have different colors, so that different needs of different users are met.

The present disclosure further provides a preparation method of any one of the nail polish glues. The method includes the following preparation steps:

S1, subjecting the acrylate prepolymer, the acrylate active monomer, the photoinitiator, and the mercaptan to mixing, heating, and stirring to obtain a first mixture;

S2, adding the additive to the first mixture, and conducting stirring for dispersion to obtain a second mixture; and S3, adding the colorant to the second mixture for color adjustment, and conducting grinding, filtration, baking at constant temperature, and standing to obtain the nail polish glue.

In one of the embodiments, in step S1, the heating is conducted at a temperature of 45-60° C., and the stirring is conducted at a rotation speed of 500-800 r/min for 10-20 minutes.

In one of the embodiments, in step S2, the stirring for dispersion is conducted at a rotation speed of 1,000-1,500 r/min, for 60-80 minutes.

In one of the embodiments, in step S3, the baking is conducted at a constant temperature of 60-80° C. for 2-4 hours.

The present disclosure provides application of any one of the nail polish glues in beautifying of nails. The nail polish glue is used in beautifying of nails.

The nail polish glue of the present disclosure and the preparation method thereof are described below in specific embodiments.

Example 1

A nail polish glue includes the following components in parts by weight: 15 parts of aliphatic carbamate acrylate, 30 parts of hydroxyethyl methacrylate, 22 parts of dipropylene glycol diacrylate, 10 parts of acylphosphorus oxide, 10 parts of pentaerythritol tetra(3-mercaptopropionate), 2 parts of an anti-settling agent, 1 part of a leveling agent, 2 parts of microcrystalline cellulose, and 8 parts of a colorant CI 77491.

A preparation method of the nail polish glue includes the following steps:

S1, adding the aliphatic carbamate acrylate, the hydroxyethyl methacrylate, the acylphosphorus oxide, and the pentaerythritol tetra(3-mercaptopropionate) to a reactor, conducting heating to 60° C., and conducting stirring at a speed of 800 r/min for 10 minutes to obtain a first mixture;

S2, after the rotation speed is reduced to 200 r/min, adding the anti-settling agent, the leveling agent, and the microcrystalline cellulose to the first mixture, and after the rotation speed is increased to 1,500 r/min, conducting stirring for dispersion for 60 minutes to obtain a second mixture; and S3, subjecting the second mixture to defoaming filtration for qualified inspection, adding the colorant for color adjustment, and conducting grinding with a three-roller machine, filtration, baking in a constant-temperature oven at a constant temperature of 80° C. for 2 hours, and standing to obtain the nail polish glue.

Example 2

A nail polish glue includes the following components in parts by weight: 37 parts of aliphatic carbamate acrylate, 20 parts of pure acrylate, 20 parts of hydroxyethyl methacrylate, 5 parts of acylphosphorus oxide, 5 parts of pentaerythritol tetra(3-mercaptopropionate), 4 parts of an anti-settling agent, 3 parts of a leveling agent, 3 parts of a defoaming agent, and 3 parts of a colorant CI 77491.

A preparation method of the nail polish glue includes the following steps:

S1, adding the aliphatic carbamate acrylate, the pure acrylate, the hydroxyethyl methacrylate, the acylphosphorus oxide, and the pentaerythritol tetra(3-mercaptopropionate) to a reactor, conducting heating to 45° C., and conducting stirring at a speed of 500 r/min for 20 minutes to obtain a first mixture;

S2, after the rotation speed is reduced to 200 r/min, adding the anti-settling agent, the leveling agent, and the defoaming agent to the first mixture, and after the rotation speed is increased to 1,000 r/min, conducting stirring for dispersion for 80 minutes to obtain a second mixture; and S3, subjecting the second mixture to defoaming filtration for qualified inspection, adding the colorant for color adjustment, and conducting grinding with a three-roller machine, filtration, baking in a constant-temperature oven at a constant temperature of 60° C. for 4 hours, and standing to obtain the nail polish glue.

Example 3

A nail polish glue includes the following components in parts by weight: 36 parts of aliphatic carbamate acrylate, 20 parts of hydroxyethyl methacrylate, 10 parts of acylphosphorus oxide, 5 parts of pentaerythritol tetra(3-mercaptopropionate), 3 parts of an anti-settling agent, 2.5 parts of a dispersing agent, 2 parts of a leveling agent, and 5 parts of a colorant CI 77492.

A preparation method of the nail polish glue includes the following steps:

S1, adding the aliphatic carbamate acrylate, the hydroxyethyl methacrylate, the acylphosphorus oxide, and the pentaerythritol tetra(3-mercaptopropionate) to a reactor, conducting heating to 52° C., and conducting stirring at a speed of 650 r/min for 15 minutes to obtain a first mixture;

S2, after the rotation speed is reduced to 200 r/min, adding the anti-settling agent, the dispersing agent, and the leveling agent to the first mixture, and after the rotation speed is increased to 1,250 r/min, conducting stirring for dispersion for 70 minutes to obtain a second mixture; and S3, subjecting the second mixture to defoaming filtration for qualified inspection, adding the colorant for color adjustment, and conducting grinding with a three-roller machine, filtration, baking in a constant-temperature oven at a constant temperature of 70° C. for 3 hours, and standing to obtain the nail polish glue.

Example 4

A nail polish glue includes the following components in parts by weight: 20 parts of polyester acrylate, 36 parts of acryloyl morpholine, 10 parts of 1-benzoylcyclohexanol, 5 parts of trimethylolpropane tris(3-mercaptopropionate), 2 parts of an anti-settling agent, 1 part of microcrystalline cellulose, 2 parts of a leveling agent, 3 parts of a defoaming agent, and 5.5 parts of a colorant CI 77492.

A preparation method of the nail polish glue includes the following steps:

S1, adding the polyester acrylate, the acryloyl morpholine, the 1-benzoylcyclohexanol, and the trimethylolpropane tris(3-mercaptopropionate) to a reactor, conducting heating to 50° C., and conducting stirring at a speed of 600 r/min for 10 minutes to obtain a first mixture;

S2, after the rotation speed is reduced to 200 r/min, adding the anti-settling agent, the microcrystalline cellulose, the leveling agent, and the defoaming agent to the first mixture, and after the rotation speed is increased to 1,300 r/min, conducting stirring for dispersion for 65 minutes to obtain a second mixture; and S3, subjecting the second mixture to defoaming filtration for qualified inspection, adding the colorant for color adjustment, and conducting grinding with a three-roller machine, filtration, baking in a constant-temperature oven at a constant temperature of 65° C. for 3 hours, and standing to obtain the nail polish glue.

Example 5

A nail polish glue includes the following components in parts by weight: 30 parts of polyester acrylate, 40 parts of acryloyl morpholine, 8 parts of 1-benzoylcyclohexanol, 5 parts of trimethylolpropane tris(3-mercaptopropionate), 2 parts of an anti-settling agent, 2 parts of a leveling agent, 2 parts of microcrystalline wax, and 6 parts of a colorant CI 77510.

A preparation method of the nail polish glue includes the following steps:

S1, adding the polyester acrylate, the acryloyl morpholine, the 1-benzoylcyclohexanol, and the trimethylolpropane tris(3-mercaptopropionate) to a reactor, conducting heating to 50° C., and conducting stirring at a speed of 600 r/min for 10 minutes to obtain a first mixture;

S2, after the rotation speed is reduced to 200 r/min, adding the anti-settling agent, the leveling agent, and the microcrystalline wax to the first mixture, and after the rotation speed is increased to 1,300 r/min, conducting stirring for dispersion for 65 minutes to obtain a second mixture; and S3, subjecting the second mixture to defoaming filtration for qualified inspection, adding the colorant for color adjustment, and conducting grinding with a three-roller machine, filtration, baking in a constant-temperature oven at a constant temperature of 65° C. for 3 hours, and standing to obtain the nail polish glue.

Comparative Example 1

A nail polish glue includes the following components in parts by weight: 30 parts of aliphatic carbamate acrylate, 30 parts of polyester acrylate, 10 parts of hydroxyethyl methacrylate, 4 parts of acylphosphorus oxide, 4 parts of pentaerythritol tetra(3-mercaptopropionate), 2 parts of an anti-settling agent, 2 parts of a leveling agent, 2 parts of microcrystalline cellulose, and 8 parts of a colorant CI 77491.

A preparation method of the nail polish glue is the same as that in Example 1.

Various properties in Examples 1-5 and Comparative Example 1 are tested according to the following methods.

(1) Surface dryness test: The solid colored polish glue developed by the present disclosure was applied flat on a glue cover, the applying thickness was controlled, the glue cover was subjected to irradiation under a 36 W UV/LED lamp for 60 seconds to carry out a photocuring reaction, the colored polish glue was detected by a finger contact method to obtain the surface dryness degree, and that is to say, after the irradiation was completed, the surface of the colored polish glue after curing was pressed by a finger. When the surface is completely not sticky to the finger, it is indicated that the surface of the colored polish glue is completely dry. The surface dryness includes 0-5 levels, level 0 indicates that the surface is not completely dry, and level 5 indicates that the surface is completely dry.

(2) Hardness test: A plastic ring was put on a flat PP surface, the solid colored polish glue developed by the present disclosure was applied in the plastic ring, the plastic ring was subjected to irradiation under a 1,000 W UV lamp at an exposure dose of 1,000 mj and then cooled for 5 minutes, and a sample was removed from the plastic ring and tested by a Shore hardness tester to obtain the hardness. A larger number indicates that the hardness is better.

(3) Leveling property test: The solid colored polish glue developed by the present disclosure was applied to a nail plate, followed by standing for 1-2 minutes, and then the surface smoothness was observed.

(4) Flexibility test: A washing-free seal developed by the present disclosure was applied, cured, and tested to obtain the thickness, and then the flexibility was tested by a cylindrical bending tester. A sample facing downward was inserted between a shaft rod and an adjusting handle and fixed. Then, the adjusting handle was stably lifted within 1-2 seconds. After that, the sample was taken out and observed to obtain the damage degree, and the flexibility of the sample was judged. According to test results, a smaller number indicates that the flexibility is better.

(5) Storage stability test: The solid colored polish glue developed by the present disclosure was put into a constant-temperature oven for an accelerated aging test at 60° C. After the test was carried out for 15 days, the glue was taken out and cooled to normal temperature, and whether the glue had abnormal phenomena, such as viscosity decline, layering, pigment sinking, substance precipitation and caking was observed. When the glue is not changed greatly, the glue is qualified, and on the contrary, the glue is not qualified.

Test results are as shown in the following Table 1.

TABLE 1

Test results of various properties in Examples 1-5 and Comparative Example 1

| Treatment | State | Surface dryness | Shore hardness (HD) | Leveling property | Flexibility (Dmm) | Storage stability |
|---|---|---|---|---|---|---|
| Example 1 | Solid | 5 | 75 | Good | 7 | Qualified |
| Example 2 | Solid | 5 | 73 | Good | 6 | Qualified |
| Example 3 | Solid | 5 | 78 | Good | 8 | Qualified |
| Example 4 | Solid | 5 | 75 | Good | 7 | Qualified |
| Example 5 | Solid | 5 | 73 | Good | 6 | Qualified |
| Comparative Example 1 | Fluid | 3 | 65 | Good | 7 | Qualified |

From the above test results of various properties, it can be concluded that a solid nail polish glue with high thixotropy and a good leveling property can be obtained only when raw materials are used in appropriate dosage ranges. Through reasonable collocation and mutual complement of the amount of components, the nail polish glue of this application can be directly applied without using a primer and a seal. Moreover, the nail polish glue has the adhesion of the primer and the gloss retention of the seal, and is convenient to operate. The nail polish glue is solid and convenient to package and transport, so that the risk of leakage is avoided. Under stirring of an external force, the viscosity of the glue can be rapidly reduced. The glue is convenient to apply, and has a good leveling property, a mirror leveling effect after being applied, and a high curing speed. A cured film has adhesion on nails and high gloss and color retention.

The above embodiments are merely preferred embodiments of the present disclosure, and are not intended to limit the protection scope of the present disclosure. Any immaterial changes and substitutions made by a person skilled in the art on the basis of the present disclosure shall fall within the protection scope as required by the present disclosure.

What is claimed is:

1. A thixotropic nail polish glue that is solid and does not flow in the absence of external force, comprising the following components in parts by weight: 15-57 parts of an acrylate prepolymer; 20-52 parts of an acrylate active monomer; 5-10 parts of a photoinitiator; 5-10 parts of mercaptan; 5-10 parts of an additive system comprising (i) an anti-settling agent comprising fumed silica, (ii) a dispersing agent, (iii) a leveling agent, and (iv) microcrystalline cellulose and/or microcrystalline wax; and 3-8 parts of a colorant.

2. The thixotropic nail polish glue according to claim 1, wherein the acrylate prepolymer is at least one selected from the group consisting of polyurethane acrylate, pure acrylate, and polyester acrylate.

3. The thixotropic nail polish glue according to claim 1, wherein the acrylate active monomer is at least one selected from the group consisting of hydroxyethyl methacrylate, acryloyl morpholine, isobornyl acrylate, dipropylene glycol diacrylate, 1,6-hexadiol diacrylate, and cyclic trimethylopropane formal acrylate.

4. The thixotropic nail polish glue according to claim 1, wherein the photoinitiator is at least one selected from the group consisting of acylphosphorus oxide, 1-benzoylcyclohexanol, 2-methyl-1-(4-methylthiophenyl)-2-morpholine-1-acetone, and ethyl (2,4,6-trimethylbenzoyl)phenylphosphinate.

5. The thixotropic nail polish glue according to claim 1, wherein the mercaptan is at least one selected from the group consisting of pentaerythritol tetra(3-mercaptopropionate), trimethylolpropane tris(3-mercaptopropionate), and 1,4-butanediol di(3-mercaptopropionate).

6. The thixotropic nail polish glue according to claim 1, wherein the additive system comprises i) an anti-settling agent comprising fumed silica, ii) a dispersing agent, iii) a leveling agent, iv) microcrystalline cellulose and microcrystalline wax, v) a thickening agent, and vi) a defoaming agent.

7. The thixotropic nail polish glue according to claim 2, wherein the mercaptan is at least one selected from the group consisting of pentaerythritol tetra(3-mercaptopropionate), trimethylolpropane tris(3-mercaptopropionate), and 1,4-butanediol di(3-mercaptopropionate).

8. The thixotropic nail polish glue according to claim 3, wherein the mercaptan is at least one selected from the group consisting of pentaerythritol tetra(3-mercaptopropionate), trimethylolpropane tris(3-mercaptopropionate), and 1,4-butanediol di(3-mercaptopropionate).

9. The thixotropic nail polish glue according to claim 4, wherein the mercaptan is at least one selected from the group consisting of pentaerythritol tetra(3-mercaptopropionate), trimethylolpropane tris(3-mercaptopropionate), and 1,4-butanediol di(3-mercaptopropionate).

10. A preparation method of a thixotropic nail polish glue that is solid and does not flow in the absence of external force, wherein the thixotropic nail polish glue comprises the following components in parts by weight: 15-57 parts of an acrylate prepolymer; 20-52 parts of an acrylate active monomer; 5-10 parts of a photoinitiator; 5-10 parts of mercaptan; 5-10 parts of an additive system comprising (i) an anti-settling agent comprising fumed silica, (ii) a dispersing agent, (iii) a leveling agent, and (iv) microcrystalline cellulose and/or microcrystalline wax; and 3-8 parts of a colorant, wherein the preparation method comprises the following steps:

S1, subjecting the acrylate prepolymer, the acrylate active monomer, the photoinitiator, and the mercaptan to mixing, heating, and stirring to obtain a first mixture;

S2, adding the additive to the first mixture, and conducting stirring for a dispersion to obtain a second mixture; and S3, adding the colorant to the second mixture for a color adjustment, and conducting grinding, filtration, baking at a constant temperature to obtain a third mixture, and standing the third mixture to obtain the nail polish glue.

11. The preparation method of the thixotropic nail polish glue according to claim 10, wherein in step S1, the heating is conducted at a temperature of 45-60 and the stirring is conducted at a rotation speed of 500-800 r/min for 10-20 minutes; and in step S2, the stirring for the dispersion is conducted at a rotation speed of 1,000-1,500 r/min for 60-80 minutes.

12. The preparation method of the thixotropic nail polish glue according to claim 10, wherein in step S3, the baking is conducted at the constant temperature of 60-80° C. for 2-4 hours.

13. The preparation method of the thixotropic nail polish glue according to claim 10, wherein the acrylate prepolymer is at least one selected from the group consisting of polyurethane acrylate, pure acrylate, and polyester acrylate.

14. The preparation method of the thixotropic nail polish glue according to claim 10, wherein the acrylate active monomer is at least one selected from the group consisting of hydroxyethyl methacrylate, acryloyl morpholine, isobornyl acrylate, dipropylene glycol diacrylate, 1,6-hexadiol diacrylate, and cyclic trimethylopropane formal acrylate.

15. The preparation method of the thixotropic nail polish glue according to claim 10, wherein the photoinitiator is at least one selected from the group consisting of acylphosphorus oxide, 1-benzoylcyclohexanol, 2-methyl-1-(4-methylthiophenyl)-2-morpholine-1-acetone, and ethyl(2,4,6-trimethylbenzoyl)phenylphosphinate.

16. The preparation method of the thixotropic nail polish glue according to claim 10, wherein the mercaptan is at least one selected from the group consisting of pentaerythritol tetra(3-mercaptopropionate), trimethylolpropane tris(3-mercaptopropionate), and 1,4-butanediol di(3-mercaptopropionate).

17. The preparation method of the thixotropic nail polish glue according to claim 10, wherein the additive system comprises i) an anti-settling agent comprising fumed silica, ii) a dispersing agent, iii) a leveling agent, iv) microcrystalline cellulose and microcrystalline wax, v) a thickening agent, and vi) a defoaming agent.

18. The preparation method of the thixotropic nail polish glue according to claim 11, wherein in step S3, the baking is conducted at the constant temperature of 60-80° C. for 2-4 hours.

19. A method of an application of the thixotropic nail polish glue according to claim 1 in beatifying of nails.

20. The method according to claim 19, wherein the acrylate prepolymer is at least one selected from the group consisting of polyurethane acrylate, pure acrylate, and poly-ester acrylate.

\* \* \* \* \*